US010352934B2

(12) United States Patent
Godec et al.

(10) Patent No.: US 10,352,934 B2
(45) Date of Patent: Jul. 16, 2019

(54) PRELOADED TEST SUBSTRATES FOR TESTING LAL-REACTIVE SUBSTANCES, METHODS OF USE, AND METHODS OF MAKING

(71) Applicant: GENERAL ELECTRIC COMPANY, Schenectady, NY (US)

(72) Inventors: Richard Douglas Godec, Boulder, CO (US); Paul Charles Melanson, Boulder, CO (US); Matthew Kaddeland Stonesmith, Boulder, CO (US); Hong Xu, Shanghai (CN); Yan Huang, Shanghai (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/719,464

(22) Filed: Sep. 28, 2017

(65) Prior Publication Data
US 2018/0017562 A1  Jan. 18, 2018

Related U.S. Application Data

(63) Continuation of application No. 14/434,273, filed as application No. PCT/US2013/063649 on Oct. 7, 2013, now abandoned.
(Continued)

(51) Int. Cl.
*G01N 33/569* (2006.01)
*B01L 3/00* (2006.01)
(Continued)

(52) U.S. Cl.
CPC ...... *G01N 33/56911* (2013.01); *B01L 3/5027* (2013.01); *B01L 3/5085* (2013.01);
(Continued)

(58) Field of Classification Search
CPC ........ C12Q 1/04; G01N 1/40; G01N 30/6091; G01N 30/88; G01N 31/00; G01N 33/56911; G01N 33/579
(Continued)

(56) References Cited

U.S. PATENT DOCUMENTS

| 3,971,186 A | 7/1976 | Havelka |
| 4,370,413 A | 1/1983 | Neeman |

(Continued)

FOREIGN PATENT DOCUMENTS

| CA | 2156226 | 2/1996 |
| CA | 2420682 | 3/2002 |

(Continued)

OTHER PUBLICATIONS

Gee et al., (Cytotherapy. 2008. 10(4):427-435).*
(Continued)

*Primary Examiner* — Jana A Hines
(74) *Attorney, Agent, or Firm* — Wegman, Hessler & Vanderburg

(57) ABSTRACT

A test substrate for detecting a LAL-reactive substance, wherein at least a portion of said test substrate has been preloaded with at least one LAL reagent and/or at least one LAL-reactive standard. Methods of use of the test substrate are disclosed. Methods of depositing test reagents on a test substrate are also disclosed.

20 Claims, 1 Drawing Sheet

Related U.S. Application Data

(60) Provisional application No. 61/710,908, filed on Oct. 8, 2012, provisional application No. 61/710,903, filed on Oct. 8, 2012, provisional application No. 61/710,990, filed on Oct. 8, 2012, provisional application No. 61/710,898, filed on Oct. 8, 2012.

(51) Int. Cl.
  *G01N 33/579* (2006.01)
  *G01N 21/17* (2006.01)

(52) U.S. Cl.
  CPC ........ *B01L 3/502715* (2013.01); *G01N 21/17* (2013.01); *G01N 33/579* (2013.01); *B01L 2200/0605* (2013.01); *B01L 2200/0684* (2013.01); *B01L 2300/021* (2013.01); *B01L 2300/087* (2013.01); *B01L 2300/0816* (2013.01); *B01L 2300/0829* (2013.01); *B01L 2300/0861* (2013.01); *B01L 2300/0864* (2013.01); *B01L 2300/0867* (2013.01); *B01L 2300/16* (2013.01); *B01L 2400/0406* (2013.01); *B01L 2400/0409* (2013.01); *B01L 2400/049* (2013.01); *B01L 2400/0487* (2013.01); *B01L 2400/0622* (2013.01); *B01L 2400/0688* (2013.01); *B01L 2400/0694* (2013.01); *G01N 2400/10* (2013.01); *G01N 2400/50* (2013.01); *Y10T 436/2575* (2015.01)

(58) Field of Classification Search
  USPC .......................................................... 435/34
  See application file for complete search history.

(56) References Cited

U.S. PATENT DOCUMENTS

| | | |
|---|---|---|
| 4,717,658 A | 1/1988 | Michaels |
| 4,819,713 A | 4/1989 | Weisman |
| 4,824,303 A | 4/1989 | Dinger |
| 4,879,634 A | 11/1989 | Storrow |
| 4,909,752 A | 3/1990 | Hallum |
| 5,010,444 A | 4/1991 | Storrow |
| 5,071,013 A | 12/1991 | Peterson |
| 5,220,485 A | 6/1993 | Chakrabarti |
| 5,224,016 A | 6/1993 | Weisman |
| 5,550,030 A | 8/1996 | Tanaka et al. |
| 5,571,683 A | 11/1996 | Nakajima et al. |
| 5,726,404 A | 3/1998 | Brody |
| 5,859,764 A | 1/1999 | Davis |
| 6,212,075 B1 | 4/2001 | Habing |
| 6,270,982 B1 | 8/2001 | Jordan et al. |
| 6,285,564 B1 | 9/2001 | O'Brien |
| 6,306,577 B1 | 10/2001 | Tamura |
| 6,319,469 B1 | 11/2001 | Mian |
| 6,687,130 B2 | 2/2004 | Adams |
| 6,887,130 B2 | 5/2005 | Lee |
| 6,900,019 B1 | 5/2005 | Horton |
| 7,031,167 B1 | 4/2006 | Zagoory |
| 7,180,737 B2 | 2/2007 | Straub, Jr. |
| 7,322,843 B1 | 1/2008 | Lee |
| 7,349,221 B2 | 3/2008 | Yurko |
| 7,807,448 B2 | 10/2010 | Glezer et al. |
| 8,045,332 B2 | 10/2011 | Lee |
| 2002/0027133 A1 | 3/2002 | Kellogg |
| 2002/0137218 A1 | 9/2002 | Mian et al. |
| 2002/0185183 A1 | 12/2002 | O'Connor et al. |
| 2004/0121450 A1 | 6/2004 | Pugia et al. |
| 2004/0131450 A1 | 7/2004 | Yang |
| 2004/0229349 A1 | 11/2004 | Daridon |
| 2005/0026239 A1 | 2/2005 | Castro et al. |
| 2005/0048655 A1 | 3/2005 | Novitsky et al. |
| 2005/0106066 A1 | 5/2005 | Saltsman et al. |
| 2005/0170515 A1 | 8/2005 | Moore |
| 2007/0231217 A1 | 10/2007 | Clinton et al. |
| 2007/0253169 A1 | 11/2007 | Clawser |
| 2008/0187445 A1 | 8/2008 | Gale et al. |
| 2008/0190220 A1 | 8/2008 | Backes |
| 2008/0239690 A1 | 10/2008 | Harvey |
| 2009/0139578 A1 | 6/2009 | Kim et al. |
| 2009/0238724 A1 | 9/2009 | Yamamoto |
| 2009/0311796 A1 | 12/2009 | Griss et al. |
| 2010/0330597 A1 | 12/2010 | Gransee et al. |
| 2011/0079094 A1 | 4/2011 | Gransee |
| 2011/0124132 A1 | 5/2011 | Kim et al. |
| 2011/0143364 A1 | 6/2011 | Kim et al. |
| 2011/0201049 A1* | 8/2011 | Wainwright ......... G01N 33/579 435/34 |
| 2011/0261537 A1 | 10/2011 | Sporer |
| 2012/0244607 A1 | 9/2012 | Iwamoto et al. |
| 2015/0060272 A1 | 3/2015 | Blidner et al. |
| 2015/0233917 A1 | 8/2015 | Melanson |
| 2015/0260719 A1 | 9/2015 | Godec |
| 2015/0293097 A1 | 10/2015 | Godec |

FOREIGN PATENT DOCUMENTS

| | | |
|---|---|---|
| CA | 2820483 | 7/2007 |
| CA | 2732011 | 2/2010 |
| CA | 2755276 | 9/2010 |
| CN | 1208464 | 2/1999 |
| CN | 101368967 | 2/2009 |
| CN | 101387647 | 3/2009 |
| CN | 101389960 | 3/2009 |
| CN | 101529246 | 9/2009 |
| CN | 102177439 | 9/2011 |
| CN | 102441356 | 5/2012 |
| EP | 0320154 | 6/1989 |
| EP | 0649021 | 4/1995 |
| EP | 0690308 | 1/1996 |
| EP | 0921397 | 6/1999 |
| EP | 0957366 | 11/1999 |
| EP | 1955770 | 8/2008 |
| EP | 1983347 | 10/2008 |
| JP | 6193958 | 5/1986 |
| JP | H03220456 A | 9/1991 |
| JP | 10253630 | 9/1998 |
| JP | 2001503854 | 3/2001 |
| JP | 2003533681 | 11/2003 |
| JP | 2004212120 | 7/2004 |
| JP | 2005519304 | 6/2005 |
| JP | 2005524058 | 8/2005 |
| JP | 2007501020 | 1/2007 |
| JP | 2009521686 | 6/2009 |
| JP | 2010042020 | 2/2010 |
| JP | 2012132879 | 7/2012 |
| WO | 3721090 | 6/1997 |
| WO | 9943432 | 9/1999 |
| WO | 9943432 A1 | 9/1999 |
| WO | 0187486 | 11/2001 |
| WO | 2004065930 | 8/2004 |
| WO | 2006009724 | 1/2006 |
| WO | 2006069757 | 7/2006 |
| WO | 2006070376 | 7/2006 |
| WO | 2007052648 | 5/2007 |
| WO | 2008139544 | 11/2008 |
| WO | 2009005231 | 1/2009 |
| WO | 2009105711 | 8/2009 |
| WO | 2011096782 | 8/2011 |

OTHER PUBLICATIONS

U.S. Non-final Office Action issued in connection with related U.S. Appl. No. 14/434,361 dated Oct. 26, 2016.
Gee et al., Cytotherapy, 2008, 10(4); pp. 427-435.
English translation of Chinese Office Action issued in related Chinese Application No. 201380052524.9 dated Dec. 4, 2015.
Chinese Office Action for related Chinese Application No. 201380052528.7 dated Oct. 27, 2015.
Nichols et al., "LAL review", PryoSense—PAT for WFI, Published by LONZA, Issue No. 1, pp. 1-6, 2008.
WinKQCL4, "Endotoxin Detection and Analysis Software", LONZA, Copyright, pp. 1-11, Mar. 2009.

(56) References Cited

OTHER PUBLICATIONS

Chinese Office Action for related Chinese Application No. 201380052528.7 dated Jul. 12, 2016.
U.S. Non-final Office Action corresponding to related U.S. Appl. No. 14/434,364 dated Aug. 29, 2016.
Hemker et al., "The Kinetics of Enzyme Cascade Systems General Kinetics of Enzyme Cascades", The Procedures of the Royal Society, B (Biological Sciences), vol. No. 173, pp. 411-420, 1969.
Bryant et al., "Endotoxin Contamination of Enzyme Conjugates Used in Enzyme-Linked Immunosorbent Assays", Journal of Clinical Microbiology, vol. No. 17, Issue No. 6, pp. 1050-1053, Jun. 1983.
Baines, "Endotoxin Testing", in Handbook of Microbiological Quality Control in Pharmaceuticals and Medical Devices, pp. 144-167, 2003.
Suh et al., "Feasability of On-Cihp Detection of Endotoxin by LAL Test", Biotechnology and Bioprocess Engineering, vol. No. 9, pp. 132-136, Jan. 1, 2004.
Gee et al., "A Multi-Center Comparison Study Between the Endosafe PTS(TM) Rapid Release Testing System and Traditional Test Methods for Detecting Endotoxin in Cell Therapy Products", Cythotherapy, vol. No. 10, Issue No. 4, pp. 427-435, Aug. 22, 2008.
Mitsumoto et al., "Novel Endotoxin Assay by Laser Light-Scattering Particle-Counting Method", Journal of Clinical Laboratory Analysis, vol. No. 23, Issue No. 2, pp. 117-124, Jan. 1, 2009.
Cooper et al., "Automated Endotoxin Testing Program for High-Risk Level Compounded Sterile Preparations at an Institutional Compounding Pharmacy", American Journal of Health-System Pharmacy, AJHP: Official Journal of the American Society of Health=System Pharmacists, vol. No. 67, Issue No. 4, pp. 280-286, Feb. 15, 2010.
Lonza, "Endoxtoxin Detection", Products and Services, pp. 1-36, May 1, 2010.
The United States Pharmacopeia, "Bacterial Endotoxins Test", Biological Tests and Assays, USP Chapter 85, Reissue, pp. R65-R69, Oct. 1, 2010.
European Pharmacopoeia, "2.6.14 Bacterial Endotoxins", Seventh Edition, vol. 1, No. 1, pp. 171-175, 2010.
Tsougeni et al., "Smart Polymeric Microfluidios Fabricated by Plasma Processing: Controlled Wetting, Capillary Filling and Hydrophobic Valving", The Royal Society of Chemistry vol. 10, No. 10, pp. 462-469, 2010.
Lonza, "Limulus Amebocyte Lysate (LAL) Kinetic-QCL", pp. 1-19, Jan. 1, 2011.
American National Standard, "Bacterial Endotoxins Test Methods, Routine Monitoring and Alternatives to Batch Testing" ANSI/AAMI ST72:2011, pp. 1-34, 2011.
The Japanese Pharmacopeia, "4.01 Bacterial Endotoxin Test", Sixteenth Edition, pp. 92-96, 2011.
Harwood, "3-Dimensional Compact Disc (CD), Microfluidic Platform", A Thesis, pp. 1-78, 2011.
ICH Harmonised Tripartite Guideline, "Evaluation and Recommendation of Pharmacopoeial Texts for Use in the ICH Regions of Bacterial Endotoxins Test General Chapter", Q4B Annex 14, Step 4 Version, Oct. 18, 2012.
The United States Pharmacopeia, "Transfusion and Infusion Assemblies and Similar Medical Devices", USP chapter 161, vol. No. 1, pp. 131-132, May 1, 2013.
International Search Report and Written Opinion for corresponding International Patent Application No. PCT/US2013/063625 dated Jan. 24, 2014.
International Search Report and Written Opinion for corresponding International Patent Application No. PCT/US2013/63645 dated Feb. 17, 2014.
International Search Report and Written Opinion for corresponding International Patent Application No. PCT/US2013/063649 dated Apr. 30, 2014.
International Search Report and Written Opinion for corresponding International Patent Application No. PCT/US2013/63639 dated Jun. 25, 2014.
Notification to Grant Patent Right for Invention for corresponding Chinese Application No. 201380052528.7 dated Jan. 22, 2017.
Notification of Reasons for Refusal in connection with related Japanese Patent Application No. 2015-535861 dated Feb. 27, 2018.
Notification of Reasons for Refusal in connection with related Japanese Patent Application No. 2015-535862 dated Feb. 27, 2018.
U.S. Non-final Office Action dated Jan. 9, 2018 for related U.S. Appl. No. 15/719,464, filed Sep. 28, 2017.
Chang et al., "Feasibility of on-chip detection of endotoxin by LAL test", Biotechnology and bioprocess engineering, pp. 132-136, Jan. 1, 2004.
International Invitation to Pay Additional Fees issued in connection with corresponding PCT Application No. PCT/US2013/063649 dated Feb. 17, 2014.
Office Action dated Sep. 8, 2017 for related U.S. Appl. No. 14/434,312.
Notification of Reasons for Refusal issued in connection with corresponding JP Application No. 2015-535859 dated Jul. 18, 2017.
Notification of Reasons for Refusal issued in connection with related JP Application No. 2015-535855 dated Jul. 18, 2017.
Fourth Office Action and Search issued in connection with corresponding CN Application No. 201380052524.9 dated Jul. 31, 2017.
Japanese Search Report issued in connection with related JP Application No. 2015-535862 dated Jun. 21, 2017.
Japanese Search Report issued in connection with related JP Application No. 2015-535861 dated Jun. 21, 2017.
Unofficial English Translation of Chinese Office Action issued in connection with related CN Application No. 201380052528.7 dated Jul. 12, 2016.
Unofficial English Translation of Chinese Office Action issued in connection with related CN Application No. 201380052528.7 dated Oct. 27, 2015.
This application is related to Paul Charles Melanson et al., filed Apr. 8, 2015, U.S. Appl. No. 14/434,312.
This application is related to Richard Douglas Godec et al., filed Apr. 8, 2015, U.S. Appl. No. 14/434,361.
This application is related to Richard Douglas Godec et al., filed Apr. 8, 2015, U.S. Appl. No. 14/434,273.
International Search Report and Written Opinion issued in connection with corresponding PCT Application No. PCT/US2013/038638 dated Jan. 7, 2014.
Unofficial English Translation of Chinese Office Action issued in connection with related CN Application No. 201380052524.9 dated Dec. 4, 2015.
Notice of Allowance dated May 17, 2018 for U.S. Appl. No. 14/434,312 (pp. 1-8).
Dungan et al., (Aerobiologia. 2009.25:265-273.
Stanson (2008. Endotoxin Testing by Kinetic-QCL Method. SOP#: CPL-0243. Version :1, Effective Date Apr. 30, 2008. University of Pittsburg Cancer Institute Immunologic Monitoring and Cellular Products Laboratory).
Office Action dated May 16, 2018 for related U.S. Appl. No. 15/884,347 (pp. 1-12).
This application is related to Paul Charles Melanson et al., filed Apr. 8, 2015, U.S. Appl. No. 14/434,364.
Office Action dated Nov. 19, 2018 for U.S. Appl. No. 16/133,666 (pp. 1-7).
Notice of Allowance dated Jan. 23, 2019 for U.S. Appl. No. 15/884,347 (pp. 1-8).
First Examination Report dated Jan. 31, 2019 in Indian Patent Application No. 2285/CHENP/2015.
First Examination Report dated Jan. 15, 2019 in Indian Patent Application No. 2155/CHENP/2015.

* cited by examiner

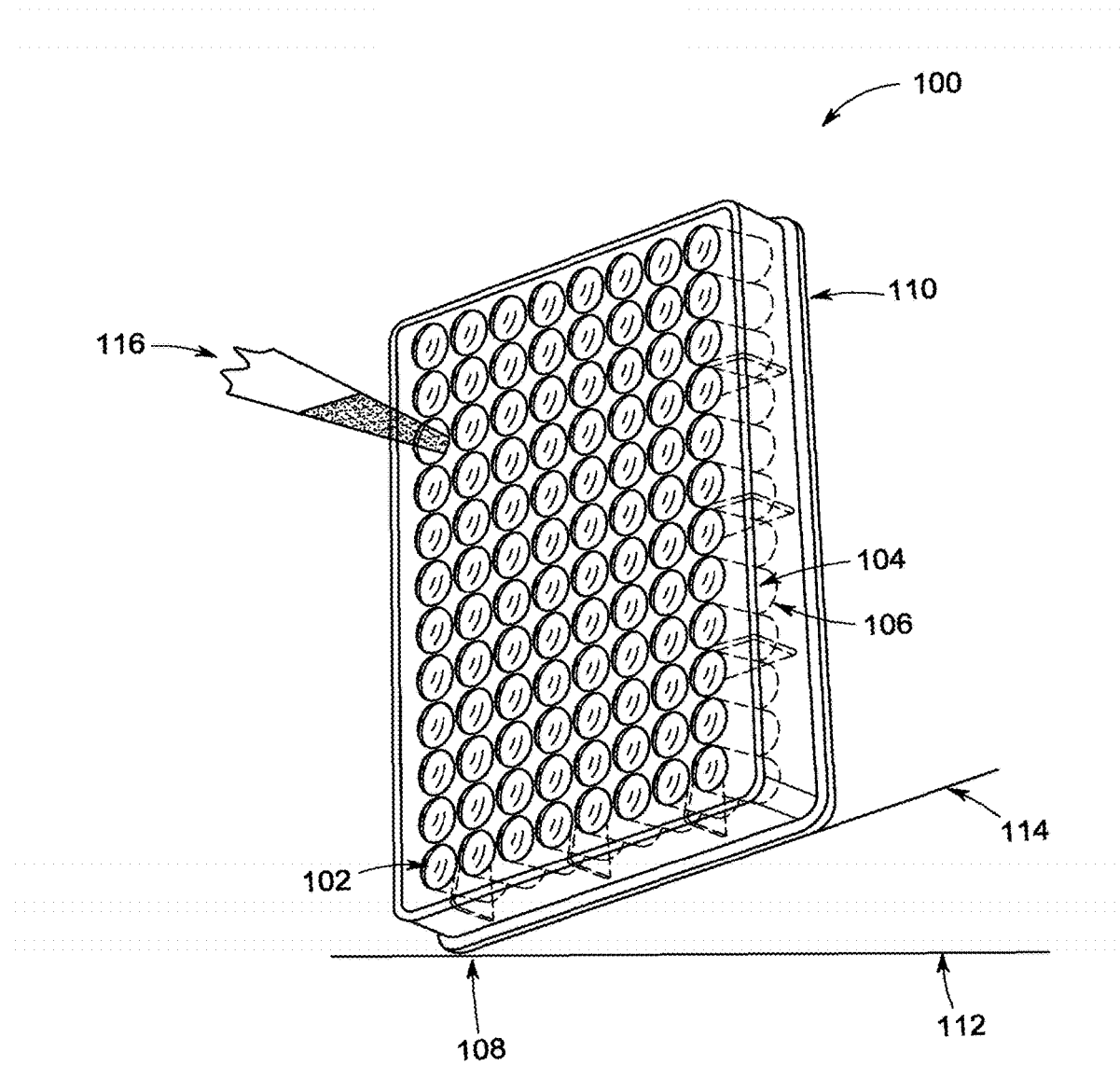

PRELOADED TEST SUBSTRATES FOR TESTING LAL-REACTIVE SUBSTANCES, METHODS OF USE, AND METHODS OF MAKING

CROSS-REFERENCE TO RELATED APPLICATIONS

This is a continuation of U.S. patent application Ser. No. 14/434,273 filed on Apr. 8, 2015, which is a national stage application under 35 U.S.C. § 371(c) of prior-filed, co-pending, PCT application serial number PCT/US2013/063649, filed on Oct. 7, 2013, which claims priority to Provisional Patent Application Ser. No. 61/710,908 filed Oct. 8, 2012 and titled MICROFLUIDIC BACTERIA ENDOTOXIN TESTING METHOD AND APPARATUS; Provisional Patent Application Ser. No. 61/710,990 filed Oct. 8, 2012 and titled CENTRIPETAL MICROFLUIDIC PLATFORM FOR BACTERIAL ENDOTOXIN TESTING; Provisional Patent Application Ser. No. 61/710,898 filed Oct. 8, 2012 and titled SENSITIVE AND RAPID METHOD FOR DETECTION OF LOW LEVELS OF ENDOTOXINS USING LAL REAGENTS; and Provisional Patent Application Ser. No. 61/710,903 filed Oct. 8, 2012 and titled MICROPLATES PRELOADED WITH ENDOTOXIN DETECTION REAGENTS WITH CALIBRATION MEANS. All of the above listed applications are herein incorporated by reference.

FIELD OF THE INVENTION

Embodiments on invention relate to the field of determining the concentration of LAL-reactive substances in a sample. More specifically, embodiments of the invention relate to preloaded test substrates and new measurement methods compatible with the United States, European, and Japanese Pharmacopeia Bacterial Endotoxins Tests ("BET") and global equivalent pharmacopeia BET standards.

BACKGROUND OF THE INVENTION

Microbial contamination, such as gram positive bacteria, gram negative bacteria, yeast, and fungi may cause severe illness and even death in humans. When people become infected with gram negative bacteria, the bacteria may produce fever-inducing bacterial endotoxins. Endotoxins can be dangerous and even deadly to humans. Endotoxin molecules, which are lipopolysaccharide components of cell walls of gram negative bacteria, can be present in drug formulations and surfaces of medical devices, independent of microbial contamination. Endotoxin contamination can happen even if a system passes a sterility test, which is why an independent endotoxin test is required.

Currently, a variety of tests have been developed to detect the presence of endotoxin in or on the sample being tested using hemocyte lysates from horseshoe crabs. Clotting will occur when the hemocyte lysate is exposed to the endotoxin. Hemocyte lysate is amebocyte lysate produced from the hemolymph of various horseshoe crab species, including the *Limulus, Tachypleus*, and *Carcinoscorpius* species. A commonly used amebocyte lysate is produced from the hemolymph of *Limulus*, or *Tachypleus* species, is referred to as *Limulus* amebocyte lysate ("LAL"). Routine tests that use LAL as a test reagent include gel clot assays, end point turbidimetric assays, kinetic turbidimetric assays, endpoint chromogenic assays, and kinetic chromogenic assays. Tests that use LAL reagent may also be used to test for glucans, a marker for fungal contamination.

More information on LAL assays and the standards used may be found in United States Pharmacopeia ("USP") Chapter 85 "Bacterial Endotoxins Test" ("BET"), Japanese Pharmacopeia 4.01 "Bacterial Endotoxin Test", European Pharmacopoeia 2.6.14 "Bacterial Endotoxins", and other equivalent national Pharmacopeias. Many of the Pharmacopeias listed above have been harmonized. Additional internationally harmonized pharmacopeia information can be found in ICH Q4B Annex 14 "Bacterial Endotoxin Test General Chapter". For endotoxin testing in medical devices, information can be found in USP Chapter 161 "Transfusion and Infusion Assemblies and Similar Medical Devices" and ANSI/AAMI ST72 "Bacterial endotoxins—Test methods, routine monitoring, and alternatives to batch testing". These standards and procedures may be generally referred to as compendia.

Manufacturers in the pharmaceutical, medical device, and food industries must meet certain standards to make sure their products do not contain microbial or endotoxin contamination. These industries require frequent, accurate, and sensitive testing for the existence of endotoxins to meet various safety standards, such as those set by the United States Food and Drug Administration, or the Environmental Protection Agency. These agencies accept many of the compendia procedures standards. Thus, if manufacturers want to obtain government approval to release a new product to market, many of the FDA requirements may be met if the products comply with the methods and standards in the compendia listed above. This can substantially reduce the cost to manufacturers to obtain FDA approval of new products.

These assays in the various compendia require aqueous solutions comprising known concentrations of an endotoxin for use as "standards". These aqueous solutions are typically unstable; therefore they are usually made from powdered toxins at the test location just prior to testing. The LAL reagent also usually comes in powder form and must be reconstituted in an aqueous solution before use.

Typically, only a few milligrams of the endotoxin and LAL powders are required, therefore accurate measurement of these powders may be tedious. Due to their fine particle size, these powders often stick to container and spatula surfaces, and are difficult to confine in the containers during testing procedures, posing additional handling problems. Using the conventional test methods, a skilled operator must manually reconstitute the endotoxin and LAL powders into endotoxin-free water while not contaminating the reagent solutions with laboratory equipment or through environmental contact.

Preparation of the endotoxin and LAL powders is difficult due to the slow solvation of the critical biological molecules and their propensity to stick to surfaces during mixing and condense on surfaces afterwards. The LAL reagent also starts reacting slowly upon reconstitution and has a very short shelf life. While the best practice would be to mix these immediately before use, workflow typically dictates mixing them at the start of the process. Also, the process of preparation is prone to contamination from endotoxins which are ubiquitous in the environment.

The agencies also require a series of calibration tests to ensure the equipment and reagents used are functioning properly. The calibration tests and sample measurements must also be made more than once. The current laboratory method of complying with BET and other compendia is very detailed and requires repetitive and highly precise measuring of fluid volumes for distribution into multiple inlets of a microplate or the like without contamination.

The most common method of performing an LAL analysis is with a microwell plate and reader. A matrix of reaction wells, open at the top and with a clear window on the bottom, are placed in a heated spectrophotometric reader used for multiple, simultaneous assays. There are many drawbacks, including the lengthy time it takes to prepare the plate, its high cost, the opportunity for mistakes and contamination, and the need to have the work done by a technician specifically trained for and dedicated to this task.

Highly skilled operators are continuously monitored to ensure proper technique and accuracy of measurement and testing, and the operators are retrained as needed so as to ensure accuracy of the repetitive actions. Typical methods may have as many as 248 slow and time consuming pipetting steps, making it an error prone method due to its complexity and contamination prone due to its length and number of manipulations.

Methods and devices have been developed to reduce the amount of steps or automated some or all of the steps in endotoxin testing. Some methods include automating one or more pipetting or aliquoting steps, automated mixing of samples, or preloading reagents in test substrates that allow only a very limited number of tests.

Other automated methods rely on robotics to measure and distribute samples and reagents in a microplate. Once prepared, the plate is loaded in a reader, either manually or using another robot. The robot is typically a pipette-based dispensing system which accurately transfers samples and reagents from a vial rack to the plate, replacing pipette tips to prevent cross-contamination. This is an expensive system which needs frequent validation of its robotic operations and may use multiple disposable, pipettes, tips, multiwell plates, dilution tubes, pipette filling trays, sampling vials, etc. for each run. It also prepares the wells in sequence, and like manual preparation, cannot start all the reactions simultaneously. Contamination is still an issue and since the process is typically unmonitored, there is no legitimate way of rejecting contaminated samples for cause.

All of the developed methods or devices, however, are missing one or more of the following aspects, low cost automation designed into the substrate, disposable clean substrate to insure cleanliness, compendial testing compliance on each substrate, built in individual test measurement validation, and simplicity of measurement operation. Accordingly, there exists a need for a more semi-automated testing method or procedure for testing and analyzing the endotoxin concentration in a fluid sample which reduces or eliminates the amount of potential operator error that complies with compendia.

BRIEF DESCRIPTION OF THE INVENTION

Accordingly, test substrates and methods are disclosed wherein the number of steps are reduced significantly, thereby minimizing contamination, timing delays and mismatches, and thus, improving accuracy. The methods are suitable for use with FDA-licensed LAL. The disclosed test substrates and measurement methods are suitable for use in pharmaceutical and biopharmaceutical manufacturing and are compatible with the United States, European, and Japanese Pharmacopeia Bacterial Endotoxins Tests and global equivalent pharmacopeia BET standards. For medical device manufacturing, the disclosed embodiments are compatible with endotoxin regulations and standards found in the international Pharmacopeia and consensus standards organizations and global equivalent standards.

Embodiments of the invention improve the standard Bacterial Endotoxins Test ("BET") by the creation of specialized test substrates with detection reagents (may be endotoxin detection reagents and/or LAL-reactive standards preloaded onto the test substrate. In one embodiment, a preloaded test substrate is disclosed wherein the preloaded test substrate has been preloaded with at least one detection reagent and/or at least one LAL-reactive standard. These preloaded test substrates may be used in tests for determining the concentration of LAL-reactive substances in an aqueous sample. As used herein LAL-reactive substance means a substance that reacts with detection reagents. Examples of LAL-reactive substances include endotoxin or 1,3-β-D-glucans such as laminarin and curdlan. LAL-reactive standards comprise LAL-reactive substances therein. The present invention may also be used with any commercial source of detection reagents. Suitable detection reagents for detecting LAL-reactive substances include Amoebocyte Lysate (*Limulus Polyphemus* or LAL and *Tachypleus Tridentatus* or TAL), Recombinant Horseshoe Crab Factor C or rFc, Monocyte Activation Type Pyrogen reagents, a mixture of recombinant Factor C and LAL, and preparations that include sushi peptides, sushi peptide fragments, sushi peptide dimers, and other specific binding proteins such as antibodies and receptor binding proteins derived from bacteriophages, and any other reagents capable of reacting with Lipid A to produce a measurable response.

The present invention may reduce the number steps the user has to perform in preparing and measuring both the calibration standards and samples. This may reduce the need for a high level of skill, experience, and training, and reduces costs, times, and the opportunity for human error. In addition embodiments of the invention may be configured or utilized in a manner that complies with compendia requirements and FDA regulations.

Embodiments of the invention are also suitable for use with all quantitative compendia photometric methods of relating the reaction progress to endotoxin levels, including 1) kinetic chromogenic, where the time until the optical absorption changes by a specified amount is related to concentration, 2) endpoint chromogenic, where the optical absorption change over a fixed time is related to concentration, 3) kinetic turbidimetric, where the time unit the turbidity (usually measured by optical absorption) changes by a specified amount is related to concentration, and 4) endpoint turbidimetric, where the turbidity change over a fixed time is related to concentration.

In another embodiment, at least a portion of the preloaded test substrate may have a modified surface. The surface may be modified using plasma etching. Alternatively, the surface may be modified using at least one coating. The coating may be a static coating, a dynamic coating, or combinations thereof. Suitable static coatings include, but are not limited to, polyethylene glycol (PEG), collagen, and combinations thereof. Suitable dynamic coatings include, but are not limited to, polyethylene glycol (PEG), sodium deoxycholate, and combinations thereof.

In yet another embodiment, the preloaded test substrate may have at least one mechanical barrier between at least one of the portions. The mechanical barrier may be soluble. The preloaded test substrate may further comprise a portion identification mechanism, such as a tracer. In another embodiment, the preloaded test substrate may be a microplate. In yet another embodiment, the preloaded test substrate may have a barrier material to protect the preloaded test substrate from environmental exposure and surface contamination.

In another embodiment, a method for measuring a LAL-reactive substance in a sample is disclosed. The method comprises contacting the sample with a preloaded test substrate wherein at least a portion of the preloaded test substrate has been preloaded with at least one detection reagent and/or at least one LAL-reactive standard, thereby making a prepared sample. An absorbance of the sample may then be measured.

In another method embodiment, at least a portion of the preloaded test substrate may have a modified surface. The surface may be modified using plasma etching. Alternatively, the surface may be modified using at least one coating. The coating may be a static coating, a dynamic coating, or combinations thereof. Suitable static coatings include, but are not limited to, polyethylene glycol (PEG), collagen, and combinations thereof. Suitable dynamic coatings include, but are not limited to, polyethylene glycol (PEG), sodium deoxycholate, and combinations thereof.

It yet another embodiment, the preloaded test substrate may be a microplate. In yet another embodiment, the preloaded test substrate may have a barrier material to protect the preloaded test substrate from environmental exposure and surface contamination.

In another embodiment, a method for depositing at least one test reagent on a microplate is disclosed. Test reagents may be any reagent that aids in testing samples. Suitable test reagents include, but are not limited to detection reagents and LAL-reactive standards. Suitable detection reagents are described above and may comprise amoebocyte lysate. LAL-reactive standards are also described above and include a USP Endotoxin Reference Standard (RSE) that has been calibrated to the current World Health Organization International Standard for Endotoxin. The method may comprise providing a test substrate having a well array comprising a plurality of wells, wherein each well has at least one optical window surface and a plurality of non-optical window surfaces. A first liquid solution having at least one detection reagent therein may be placed on a first non-optical window surface of at least one well. The first liquid solution may be dried on the first non-optical window surface thereby depositing the detection reagent on the first non-optical surface to form a preloaded test substrate.

In another embodiment, the method for depositing at least one test reagent on a test substrate may further comprise placing a second solution having at least one LAL-reactive standard therein on a second non-optical window surface. The second liquid solution may be dried on the second non-optical window surface thereby depositing the LAL-reactive standard on the second non-optical window surface.

In another embodiment, the test substrate may be a microplate. In yet another embodiment, the method may further comprise covering the preloaded test substrate with a barrier material after the drying step to protect the preloaded test substrate from environmental exposure and surface contamination.

BRIEF DESCRIPTION OF THE DRAWINGS

FIG. 1 shows an embodiment of the invention wherein a test reagent may be deposited on the sidewalls of a microplate.

DETAILED DESCRIPTION

In one embodiment, a preloaded test substrate is disclosed wherein the preloaded test substrate has been preloaded with at least one detection reagent and/or at least one LAL-reactive standard. The preloaded test substrate is designed to measure the BET in samples. It may also be used to provide calibration data from known spikes using a LAL-reactive standard. The preloaded test substrates may be designed to meet all the current BET pharmaceutical regulations requirements and may be used with turbidimetric, chromogenic, and gel-clot BET methods. The LAL-reactive standard may be endotoxin that has been calibrated to the relevant regulatory master endotoxin (CSE) and the regulatory master endotoxin standard (RSE). Where other methods are acceptable or have been validated as being equivalent and acceptable to regulatory agencies, a stored calibration based on historical data can be used instead of the results from individual standards.

Accordingly, preloaded test substrates and methods are disclosed wherein the number of testing steps are reduced significantly, thereby minimizing contamination, timing delays and mismatches, and thus, improving accuracy. The methods are suitable for use with FDA-licensed detection reagents. The methods may be used with a standard absorbance or microplate reader with built in thermal control, a mixer, and an optical reader to determine the BET results.

In another embodiment, the LAL-reactive standard may preloaded in at least three different portions of the preloaded test substrate. These three different portions may form a calibration portion. The concentration of the LAL-reactive standard in each portion may be the same or different. If endotoxin is used, the first portion may have an amount such that when an aqueous sample (or blank water) is present in that portion, the endotoxin concentration in the sample ranges from 0.005 to 0.5 EU/mL. Similarly, the second portion may have an amount corresponding to a concentration ranging from 0.05 to 5.0 EU/mL and the third portion may have an amount corresponding to a concentration ranging from 0.5 to 50 EU/mL.

In another embodiment, at least two portions of the preloaded test substrate may form a sample measurement portion. The two portions may be loaded with a LAL-reactive standard to form spikes.

The detection reagent and/or LAL-reactive standard may be deposited onto various test substrates, such as onto the sidewalls of a microplate well to allow a sample blank measurement, onto the optical window of a microplate well, onto a soluble coating, or onto an optically translucent or reflective insoluble film. Alternatively, the test reagents may be added as dried beads or coarse particles, or deposited into a carrier media that is added to the test substrate.

In another embodiment, at least a portion of the preloaded test substrate may have a modified surface. The surface may be modified using plasma etching. Alternatively, the surface may be modified using at least one coating. The coating may be a static coating, a dynamic coating, or combinations thereof. Suitable static coatings include, but are not limited to, polyethylene glycol (PEG), collagen, and combinations thereof. Suitable dynamic coatings include, but are not limited to, polyethylene glycol (PEG), sodium deoxycholate, and combinations thereof.

In yet another embodiment, the preloaded test substrate may have at least one mechanical barrier between at least one of the portions. The mechanical barrier may be soluble.

The test substrate with preloaded reagents may be packaged such it is sealed from the environment by using a barrier material that prevents moisture, bacteria, and endotoxin agents from contaminating the preloaded reagents. Accordingly, in yet another embodiment, the preloaded test substrate may have a barrier material to protect the preloaded test substrate from environmental exposure and surface contamination. In another embodiment, the preloaded test substrate may be a microplate.

Sample introduction errors may be further reduced by a plurality of optional identification mechanisms on the preloaded test substrate or in a reader configured to read or measure samples in the test substrate. The identification mechanisms may identify the sample to the user or notify the user if additional reagents are required. Suitable identifications means may include optical markers such as color markers, alphanumeric markers, or light emitting diodes. In one embodiment, the identification mechanism may be a tracer. A tracer is an inert compound that is added to a fluid to aid in determining the volume, fluid location and movement (fluid motions). The tracer may also be used to aid in validating the measurement data. Suitable tracers include, but are not limited to, dyes.

In another embodiment a method for measuring an endotoxin in a sample is disclosed. As used in this specification, the term "sample" may include not only the sample to be analyzed, but water that shows no reaction with the detection reagent or lysate employed at the detection limit. Samples of non-reactive water may also be referred to as "LAL Reagent Water", "Water for BET" or "Water for Injection".

The method may comprise contacting the sample with a preloaded test substrate wherein at least a portion of the preloaded test substrate has been preloaded with at least one detection reagent and/or at least one LAL-reactive standard, thereby making a prepared sample. An absorbance of the sample may then be measured.

The sample may contact more than one portion of the test substrate. The prepared sample contacting the preloaded test substrate may or may not come into contact with a test reagent. For example, the prepared sample may be a "blank" or negative control that does not contact any test reagent, or only comes into contact with a detection reagent. In another method, a portion of the substrate may be further preloaded with at least one LAL-reactive standard. If the LAL-reactive standard is an endotoxin standard, it may be present in a plurality of concentrations, wherein each concentration is present on a different portion of the substrate as described above. The endotoxins may be preloaded onto the substrate such that a "standard curve" may be generated as required in USP 85. In another embodiment, the plurality of endotoxin standard concentrations may be used to generate a standard curve.

In another method embodiment, at least a portion of the preloaded test substrate may have a modified surface. The surface may be modified using plasma etching. Alternatively, the surface may be modified using at least one coating. The coating may be a static coating, a dynamic coating, or combinations thereof. Suitable static coatings include, but are not limited to, polyethylene glycol (PEG), collagen, and combinations thereof. Suitable dynamic coatings include, but are not limited to, polyethylene glycol (PEG), sodium deoxycholate, and combinations thereof.

It yet another embodiment, the preloaded test substrate may be a microplate. In yet another embodiment, the preloaded test substrate may have a barrier material to protect the preloaded test substrate from environmental exposure and surface contamination.

In another embodiment, a method for depositing at least one test reagent on a microplate is disclosed. Test reagents may be any reagent that aids in testing samples. Suitable test reagents include, but are not limited to detection reagents and LAL-reactive standards. Suitable detection reagents are described above and may comprise amoebocyte lysate. LAL-reactive standards are also described above and include a USP Endotoxin Reference Standard (RSE) that has been calibrated to the current World Health Organization International Standard for Endotoxin. The method may comprise providing a test substrate having a well array comprising a plurality of wells, wherein each well has at least one optical window surface and a plurality of non-optical window surfaces. A first liquid solution having at least one detection reagent therein may be placed on a first non-optical window surface of at least one well. The first liquid solution may be dried on the first non-optical window surface thereby depositing the detection reagent on the first non-optical surface to form a preloaded test substrate. The LAL-reactive standard may be present in a plurality of concentrations, wherein each concentration is present in a separate well of the test substrate.

In another embodiment, the method for depositing at least one test reagent on a test substrate may further comprise placing a second solution having at least one LAL-reactive standard therein on a second non-optical window surface. The second liquid solution may be dried on the second non-optical window surface thereby depositing the LAL-reactive standard on the second non-optical window surface.

In another embodiment, the test substrate may be a microplate. In yet another embodiment, the method may further comprise covering the preloaded test substrate with a barrier material after the drying step to protect the preloaded test substrate from environmental exposure and surface contamination. Suitable test substrates include any test substrate that aids in evaluating or testing a sample, such as microplates available from Sigma-Aldrich, or microtiter plates. As shown in FIG. 1, the microplate (100) may have multiple sample wells (102) arranged in a 2 by 3 rectangular matrix. Microplates typically have 6, 24, 96, 384, or 1536 wells. In one embodiment, the microplate (100) may have 96 wells (102). Although the holding capacity of individual wells within one microplate is usually the same, the holding capacity of the wells may vary from microplate to microplate. The sidewalls (104) and bottoms (106) of the wells (102) may be curved or straight, such that the wells are semi-spherical, cylindrical, or rectangular in shape. The plate may also comprise a substantially planar bottom surface (108) such that the microplate rests flat on working surfaces. Working surfaces may include, but are not limited to, the ground, lab bench tops, microplate readers, and heating plates, as well as manufacturing surfaces such as, tables, conveyors, and rollers. It is also possible that the microplate does not rest on a working surface at all, but is suspended above the working surface via a suspension means such as hooks, clips, etc. The microplate may be made of a variety of materials, including polystyrene and polypropylene, or polycarbonate. An optical detection microplate may be made with polystyrene or other suitable polymer that does not interfere with the chemical performance of the test reagents with the sample. In some embodiments, titanium dioxide may be added to make the polystyrene white to aid in optical absorbance methods.

One or more portions of the test substrate may have modified surfaces. The portions with modified surfaces may include, but are not limited to, the sidewalls and wells. The surfaces may be modified by any means known to those of ordinary skill in the art, including but not limited to, applying a coating, radiation, plasma etching, UV light and ozone, or dissolved reagents which may dynamically cover the surface, so that the interaction of the surfaces and reagents or samples mimic that of standard microplate analysis so that the manufacturer's specifications or compendia standards for analysis are met.

In one embodiment, the surfaces of the test substrate may be modified to control the biochemical LAL and LAL-reactive substance interaction or to control the surface energy. Controlling the level of the surface chemical interaction with the reaction chemistries may improve the repeatability and accuracy of the biochemical performance. For example, materials suitable for manufacturing the test substrates may also biochemically inhibit or enhance the LAL or LAL-reactive substance reaction chemistry. This biochemical interaction between the material surface and the reaction chemistries may be controlled or reduced with the application of a coating or through a chemical modification of the surface. Additionally, the unmodified surface of the test substrates may have an undesirable surface energy for the microfluidics present on the test substrate. The surface energy may also be modified to a desired value through chemical modification or the addition of a coating to make the surface energy more hydrophilic or more hydrophobic, or to achieve any other surface energy between these states. By optimizing the surface energy, the microfluidics present on the test substrate may also be optimized.

Another means to modify test substrate surfaces include plasma etching, where the surface is modified by having it exposed to plasma to affect a particular final surface chemical structure. Different elements may be added to the plasma to modify the chemistry of the surface, for example, oxygen or ammonia. Additional means include the use of permanent static or dynamic surface coatings. Static surface coatings may be added to form a layer on the test substrate surface to change the surface character. Static surface coatings may be applied as a solution with a solvent and dried or applied by surface grafting wherein the coating is chemically bonded to the surface. Examples of static coatings that may be grafted or applied as a coating include, but are not limited to, polyethylene glycol (PEG) and collagen. Dynamic surface coatings may be added to the reagents, samples, or standards and coat the surface in situ as fluids move on the test substrate or in sample wells. Examples of dynamic coatings include, but are not limited to PEG and surfactants like sodium deoxycholate.

In one embodiment, the method may comprise providing a microplate having a well array comprising a plurality of wells, wherein each well has at least one optical window surface and a plurality of non-optical window surfaces; providing a liquid solution having at least one test reagent therein; placing the liquid solution on a first of said non-optical window surfaces of at least one well; and drying the liquid solution on the first non-optical window surface, thereby depositing the test reagent on the first non-optical window surface. In another embodiment, the deposition steps may be repeated on subsequent non-optical window surfaces such that additional test reagents are deposited on subsequent sidewall portions.

The test reagents may be added to non-optical window surfaces of the well, to allow an initial optical measurement of the sample before the test reagents have had a chance to mix. This is useful for determining the optical zero. In addition, each test reagent has an optical signature that may be used to check that the correct levels of test reagents are added, prior to the reaction beginning. In another embodiment, each test reagent may be tagged with an optical material that is inert to the endotoxin test reaction. If the user finds incorrect levels of the expected levels of test reagents prior to the reaction taking place (reaction lag phase period), then the user may reject the measurement test for that sample. This is of great value to the pharmaceutical user, as any Out Of Specification (OOS) test must be evaluated and explained.

In another method embodiment, the method may comprise providing a liquid solution having at least one test reagent therein; providing a microplate having a substantially planer bottom surface, a plurality of edges (110), and a well array, wherein the bottom surface is substantially parallel with respect to a horizontal working surface (112), and wherein the well array comprises a plurality of wells having a plurality of sidewalls. A first of the plurality of edges (110) may be tilted such that the first edge is inclined (114) in a generally perpendicular orientation with respect to the horizontal working surface, such that the bottom surface is no longer substantially parallel with respect to the working surface and such that a sidewall portion closest to the working surface is in a generally parallel orientation with respect to the working surface. The liquid solution may be placed (116) on the sidewall portion and then dried, thereby depositing the test reagent on the sidewall portion. Any means suitable to transferring a liquid may be suitable, including, but not limited to, a pipette, or a spray nozzle.

Any drying process is suitable for the present invention, as long as the drying process does not alter the reactivity of the test reagents. These drying processes include, but are not limited to, a vacuum drying process at ambient temperature or a freeze drying process (lyophilization). In yet another embodiment, the liquid solution may be dried at ambient temperature or freeze dried. It should be understood that the liquid solution need not be dried completely; it may be partially dried, especially if non-aqueous solvents are used. It is sufficient that the test reagent is physically immobilized after it is deposited such that it remains in place. There may be some liquid still present after the test reagent is immobilized if a glycerin paste is used, as in certain pharmaceuticals and other materials prepared for stable storage. The same process may be used with both round-walled and flat-walled wells. The tilt-position of the microplate may be maintained during the deposition steps through the use of a supporting means such as a stand or brace.

In another embodiment, the microplate may be rotated and the deposition steps may be repeated with subsequent edges of the microplate such that additional test reagents are deposited on subsequent sidewall portions. In another method embodiment, at least one test reagent comprising an endotoxin detection reagent may be present in every well. In another method embodiment, at least one test reagent compromises an endotoxin standard. In yet another method embodiment, the endotoxin standard may be present in a plurality of concentrations, wherein each concentration is present in a different well. In yet another method embodiment, the microplate may further comprise a well identification mechanism.

Many approaches to the test reagent deposition may be used to reduce mixing time, bubble formation, resolubilization time, ease of manufacturing, and detection sensitivity. The approaches may encompass both chemical and physical means to produce the desired results. Chemical means may include the use of chemical additives. Examples of chemical additives include solubility enhancing agents, such as the saccharides sucrose, glucose, and mannitol, as well as anti-flaking agents, such as aqueous polymer solutions comprising poly(ethylene oxide), hydroxypropyl cellulose, or hydroxypropyl methyl cellulose, or agents designed to prevent degradation such as dextran and various saccharides such as lactose and trehalose. Physical means may include various coating, spraying, or drying techniques during the deposition process.

In some embodiments, a detection reagent may be deposited in every well. Alternatively, there is no detection reagent in any of the wells, allowing the user to add detection reagent from a preferred supplier. In one embodiment, the detection reagent may be amoebocyte lysate. The use of the natural absorption of LAL, or the addition of turbidimetric or chromogenic non-LAL reactive tracers to the LAL and endotoxin may also be used to reduce testing errors.

The LAL-reactive standard may be deposited in only a portion of the wells. In addition, various wells may be preloaded or predeposited with LAL-reactive standard with different concentrations of the LAL-reactive substance therein, such that the user merely has to add the sample to be tested to the wells. In one embodiment, the detection reagent and LAL-reactive substance may be deposited in the wells such that all of the tests and replicates required by USP 85 may be performed simply by adding the samples. In such an embodiment, each well comprises either a separate given test, or a replicate of a given test. In one embodiment, the lowest concentration may be confirmed in four replicates, wherein 4 of the 96 wells each comprise one replicate. Alternatively, the wells may be preloaded with LAL-reactive standards such that the inhibition/enhancement tests (or "spikes"), including replicates, may be performed. Alternatively, the wells may be preloaded such that the quantitative tests, wherein the concentration of bacterial endotoxins in a given sample is quantified, may be performed. In yet another embodiment, the wells may be preloaded such that all the tests and replicates required under USP 85, including the lysate sensitivity, the inhibition/enhancement, and quantitative tests, may be performed on the same microplate. Similar concepts may be employed with any test substrate or any portion of a test substrate and are not limited to microplates with wells.

In one embodiment, the wells may be covered with a seal means, such as an adhesive label with adhesive only on the portions of the label outside the well opening. The seal means may be made of a barrier material that prevents the passage of water and oxygen, whereby the wells may be kept dry to a humidity level less than about 5%.

The disclosed methods may be used to pre-deposit LAL reagents, chromogenic reagents and endotoxin in pre-cleaned (endotoxin free) 96 or 384-well microplates. The test reagents, in a liquid solution, may be placed on the walls of the wells, or on the optical window surface of the optical well. The liquid solution may also comprise chemical additives such as solubility enhancing agents and anti-flaking agents. The disclosed methods allow the reagents to be deposited on the walls of the standard 96 or 384-well microplates without interfering with the optical window or the optical path, thereby allowing an initial sample absorption measurement.

In another embodiment, a test substrate is disclosed wherein at least a portion of the test substrate has been preloaded with at least one test reagent. The test substrate is suitable for optical monitoring of liquids and use in performing LAL assays for endotoxins or glucans.

Reagents for the LAL assays may be isolated in segments of the test substrate. The test substrate may be disposable. The test substrate may have a variety of forms, geometries and shapes, including a typical microplate shape. Other suitable forms include, but are not limited to, cards, cartridges, or discs. The test substrate may also be configured such that samples and fluids may be added to it. The test substrate also allows for mixing of samples as the test substrate is shaken, swirled, spun or rotated. The test substrate also allows for the optical monitoring of liquids.

The test substrate can be used for performing analytical functions including, but not limited to, measurement of samples with an added positive product control that is an endotoxin or glucan spike, measurement of water blanks (free of endotoxin or LAL reagent), measurement of a series of at least three calibration solutions. Moreover, the test substrate may be used for performing all the analytical functions listed in two or more duplicates.

The test substrate may be used with an optical apparatus or reader that measures the times between optical absorption states or the optical absorption change between times. The preloaded test substrate may also be used for confirmation that the reagents and analyzer meet specifications, calibration for conversion to endotoxin or glucan concentrations in the sample, validation of performance or meeting compendia or the optical apparatus manufacturers' specifications, and measurement of the samples being analyzed.

The test substrate may be made from any suitable material. In another embodiment, portions of the test substrate may be coated with polymer materials, surface treatments, or coatings to meet compendia or the test reagent manufacturers' specifications. In yet another embodiment, a portion of the test substrate may be coated with a static coating to reduce LAL reagent or standard loss. Another portion of the test substrate may be coated with a dynamic coating of the microplate wells to reduce LAL reagent or standards loss. The dynamic coating may also be mixed with standards or reagents.

A portion of the test substrate may also be coated with additives to aid, or regulate, proper analysis and interactions of test reagents or sample materials. Exemplary additives include, but are not limited to solubility aids, transport aids, and stabilizers.

In yet another embodiment, the test substrate may comprise mechanical barriers separate reagents to prevent interaction as they are being isolated in the test substrate or being stored long-term. The barriers may be insoluble and arranged such that they do not interfere with optical measurements. Other barriers may be soluble to some extent so that they dissolve during measurement and do not interfere with it.

In yet another embodiment, the test substrate may be preloaded with standards and spikes made from control standard endotoxin (CSE) or reference standard endotoxin. The spikes may be stored as dried material so that they are at the correct concentration while not diluting or interfering with the sample being spiked.

EXAMPLE

The following example demonstrates an embodiment wherein endotoxin standards are preloaded onto the test substrate. The endotoxin standard range is shown in Table 1. The endotoxin standard range, however, may be different in other embodiments.

TABLE 1

| Range (EU/mL) | Lowest (EU/mL) | Mid Range (EU/mL) | Highest (EU/mL) |
|---|---|---|---|
| 0.005-0.5 | 0.005 | 0.05 | 0.5 |
| 0.01-1 | 0.01 | 0.1 | 1 |
| 0.05-5 | 0.05 | 0.5 | 5 |

TABLE 1-continued

| Range (EU/mL) | Lowest (EU/mL) | Mid Range (EU/mL) | Highest (EU/mL) |
|---|---|---|---|
| 0.1-10 | 0.1 | 1 | 10 |
| 0.5-50 | 0.5 | 5 | 50 |

Table 2 is a description of the preloaded test substrate, wherein the test substrate has 96 portions. Column 1 indicates the portion of the test substrate. Column 2 indicates the sample that the operator must add to the test substrate. Each portion of the test substrate may be preloaded with a different endotoxin standard concentration as shown in Column 3. Column 4 is a description of the BET test that may be completed in each portion. The endotoxin detection reagent is not shown in Table 2 as all 96 portions may be preloaded with the same amount of an endotoxin detection reagent. Alternatively, the test substrate may not have any endotoxin detection reagent, allowing the operator to add an endotoxin detection reagent from a preferred supplier.

TABLE 2

| Column 1 Substrate Portion | Column 2 Sample | Column 3 Endotoxin Standard | Column 4 Description |
|---|---|---|---|
| 1 | Water for BET | 0 | Negative Control (Blank) Rep 1 |
| 2 | Water for BET | 0 | Negative Control (Blank) Rep 2 |
| 3 | Water for BET | 0 | Negative Control (Blank) Rep 3 |
| 4 | Water for BET | Lowest | Lowest Detection Range Calibration Standard Rep 1 |
| 5 | Water for BET | Lowest | Lowest Detection Range Calibration Standard Rep 2 |
| 6 | Water for BET | Lowest | Lowest Detection Range Calibration Standard Rep 3 |
| 7 | Water for BET | Mid Range | Mid Range Calibration Standard Rep 1 |
| 8 | Water for BET | Mid Range | Mid Range Calibration Standard Rep 2 |
| 9 | Water for BET | Mid Range | Mid Range Calibration Standard Rep 3 |
| 10 | Water for BET | Highest | Highest Detection Range Calibration Standard Rep 1 |
| 11 | Water for BET | Highest | Highest Detection Range Calibration Standard Rep 2 |
| 12 | Water for BET | Highest | Highest Detection Range Calibration Standard Rep 3 |
| 13 | Sample A | 0 | Sample A Analysis Rep 1 |
| 14 | Sample A | 0 | Sample A Analysis Rep 2 |
| 15 | Sample A | Mid Range | Positive Control Spike for Sample A Rep 1 |
| 16 | Sample A | Mid Range | Positive Control Spike for Sample A Rep 2 |
| 17 | Sample B | 0 | Sample B Analysis Rep 1 |
| 18 | Sample B | 0 | Sample B Analysis Rep 2 |
| 19 | Sample B | Mid Range | Positive Control Spike for Sample B Rep 1 |
| 20 | Sample B | Mid Range | Positive Control Spike for Sample B Rep 2 |
| 21 | Sample C | 0 | Sample C Analysis Rep 1 |
| 22 | Sample C | 0 | Sample C Analysis Rep 2 |
| 23 | Sample C | Mid Range | Positive Control Spike for Sample C Rep 1 |
| 24 | Sample C | Mid Range | Positive Control Spike for Sample C Rep 2 |
| 25 | Sample D | 0 | Sample D Analysis Rep 1 |
| 26 | Sample D | 0 | Sample D Analysis Rep 2 |
| 27 | Sample D | Mid Range | Positive Control Spike for Sample D Rep 1 |
| 28 | Sample D | Mid Range | Positive Control Spike for Sample D Rep 2 |
| 29 | Sample E | 0 | Sample E Analysis Rep 1 |
| 30 | Sample E | 0 | Sample E Analysis Rep 2 |
| 31 | Sample E | Mid Range | Positive Control Spike for Sample E Rep 1 |
| 32 | Sample E | Mid Range | Positive Control Spike for Sample E Rep 2 |
| 33 | Sample F | 0 | Sample F Analysis Rep 1 |
| 34 | Sample F | 0 | Sample F Analysis Rep 2 |
| 35 | Sample F | Mid Range | Positive Control Spike for Sample F Rep 1 |
| 36 | Sample F | Mid Range | Positive Control Spike for Sample F Rep 2 |
| 37 | Sample G | 0 | Sample G Analysis Rep 1 |
| 38 | Sample G | 0 | Sample G Analysis Rep 2 |
| 39 | Sample G | Mid Range | Positive Control Spike for Sample G Rep 1 |
| 40 | Sample G | Mid Range | Positive Control Spike for Sample G Rep 2 |
| 41 | Sample H | 0 | Sample H Analysis Rep 1 |
| 42 | Sample H | 0 | Sample H Analysis Rep 2 |
| 43 | Sample H | Mid Range | Positive Control Spike for Sample H Rep 1 |
| 44 | Sample H | Mid Range | Positive Control Spike for Sample H Rep 2 |
| 45 | Sample I | 0 | Sample I Analysis Rep 1 |
| 46 | Sample I | 0 | Sample I Analysis Rep 2 |
| 47 | Sample I | Mid Range | Positive Control Spike for Sample I Rep 1 |
| 48 | Sample I | Mid Range | Positive Control Spike for Sample I Rep 2 |
| 49 | Sample J | 0 | Sample J Analysis Rep 1 |
| 50 | Sample J | 0 | Sample J Analysis Rep 2 |
| 51 | Sample J | Mid Range | Positive Control Spike for Sample J Rep 1 |
| 52 | Sample J | Mid Range | Positive Control Spike for Sample J Rep 2 |
| 53 | Sample K | 0 | Sample K Analysis Rep 1 |
| 54 | Sample K | 0 | Sample K Analysis Rep 2 |
| 55 | Sample K | Mid Range | Positive Control Spike for Sample K Rep 1 |
| 56 | Sample K | Mid Range | Positive Control Spike for Sample K Rep 2 |
| 57 | Sample L | 0 | Sample L Analysis Rep 1 |
| 58 | Sample L | 0 | Sample L Analysis Rep 2 |
| 59 | Sample L | Mid Range | Positive Control Spike for Sample L Rep 1 |
| 60 | Sample L | Mid Range | Positive Control Spike for Sample L Rep 2 |
| 61 | Sample M | 0 | Sample M Analysis Rep 1 |
| 62 | Sample M | 0 | Sample M Analysis Rep 2 |
| 63 | Sample M | Mid Range | Positive Control Spike for Sample M Rep 1 |
| 64 | Sample M | Mid Range | Positive Control Spike for Sample M Rep 2 |
| 65 | Sample N | 0 | Sample N Analysis Rep 1 |
| 66 | Sample N | 0 | Sample N Analysis Rep 2 |
| 67 | Sample N | Mid Range | Positive Control Spike for Sample N Rep 1 |
| 68 | Sample N | Mid Range | Positive Control Spike for Sample N Rep 2 |
| 69 | Sample O | 0 | Sample O Analysis Rep 1 |
| 70 | Sample O | 0 | Sample O Analysis Rep 2 |
| 71 | Sample O | Mid Range | Positive Control Spike for Sample O Rep 1 |
| 72 | Sample O | Mid Range | Positive Control Spike for Sample O Rep 2 |
| 73 | Sample P | 0 | Sample P Analysis Rep 1 |
| 74 | Sample P | 0 | Sample P Analysis Rep 2 |
| 75 | Sample P | Mid Range | Positive Control Spike for Sample P Rep 1 |
| 76 | Sample P | Mid Range | Positive Control Spike for Sample P Rep 2 |
| 77 | Sample Q | 0 | Sample Q Analysis Rep 1 |
| 78 | Sample Q | 0 | Sample Q Analysis Rep 2 |
| 79 | Sample Q | Mid Range | Positive Control Spike for Sample Q Rep 1 |

TABLE 2-continued

| Column 1 Substrate Portion | Column 2 Sample | Column 3 Endotoxin Standard | Column 4 Description |
|---|---|---|---|
| 80 | Sample Q | Mid Range | Positive Control Spike for Sample Q Rep 2 |
| 81 | Sample R | 0 | Sample R Analysis Rep 1 |
| 82 | Sample R | 0 | Sample R Analysis Rep 2 |
| 83 | Sample R | Mid Range | Positive Control Spike for Sample R Rep 1 |
| 84 | Sample R | Mid Range | Positive Control Spike for Sample R Rep 2 |
| 85 | Sample S | 0 | Sample S Analysis Rep 1 |
| 86 | Sample S | 0 | Sample S Analysis Rep 2 |
| 87 | Sample S | Mid Range | Positive Control Spike for Sample S Rep 1 |
| 88 | Sample S | Mid Range | Positive Control Spike for Sample S Rep 2 |
| 89 | Sample T | 0 | Sample T Analysis Rep 1 |
| 90 | Sample T | 0 | Sample T Analysis Rep 2 |
| 91 | Sample T | Mid Range | Positive Control Spike for Sample T Rep 1 |
| 92 | Sample T | Mid Range | Positive Control Spike for Sample T Rep 2 |
| 93 | Sample U | 0 | Sample U Analysis Rep 1 |
| 94 | Sample U | 0 | Sample U Analysis Rep 2 |
| 95 | Sample U | Mid Range | Positive Control Spike for Sample U Rep 1 |
| 96 | Sample U | Mid Range | Positive Control Spike for Sample U Rep 2 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. For example, there are many other approaches to depositing the reagents without intermixing the LAL and endotoxin and causing premature reaction. Such other approaches are intended to be within the scope of the claims if they have structural elements that do not differ from the literal language of the claims, or if they include equivalent structural elements with insubstantial differences from the literal languages of the claims.

The invention claimed is:

1. A preloaded test substrate for detecting a LAL-reactive substance, wherein at least a portion of said preloaded test substrate has been preloaded with:
   at least one LAL-reactive standard, or
   at least one detection reagent and at least one LAL-reactive standard;
   wherein said LAL-reactive standard is present in at least two different concentrations and each concentration is present on a separate portion of said preloaded test substrate.

2. The preloaded test substrate of claim 1, wherein at least a portion of said preloaded test substrate has a modified surface.

3. The preloaded test substrate of claim 2, wherein said modified surface is modified using plasma etching.

4. The preloaded test substrate of claim 2, wherein said modified surface is modified using at least one coating, wherein said coating is a static coating, dynamic coating, or combinations thereof.

5. The preloaded test substrate of claim 4, wherein at least one static coating is selected from the group consisting of polyethylene glycol (PEG), collagen, and combinations thereof.

6. The preloaded test substrate of claim 4, wherein at least one dynamic coating is selected from the group consisting of polyethylene glycol (PEG), sodium deoxycholate, and combinations thereof.

7. The preloaded test substrate of claim 1, further comprising at least one mechanical barrier between at least one of said separate portions.

8. The preloaded test substrate of claim 7, wherein at least one mechanical barrier is soluble.

9. The preloaded test substrate of claim 1, wherein said preloaded test substrate further comprises a portion identification mechanism.

10. The preloaded test substrate of claim 1, wherein said preloaded test substrate is a microplate.

11. The preloaded test substrate of claim 1, wherein said preloaded test substrate further comprises a barrier material to protect said preloaded test substrate from environmental exposure and surface contamination.

12. A method for measuring a LAL-reactive substance in a sample, said method comprising:
   (a) contacting said sample with a preloaded test substrate wherein at least a portion of said preloaded test substrate has been preloaded with:
      at least one LAL-reactive standard, or
      at least one detection reagent and at least one LAL-reactive standard;
      wherein said LAL-reactive standard is present in at least two different concentrations, and each concentration is present on a separate portion of said test substrate, thereby making a prepared sample; and
   (b) measuring an absorbance of said prepared sample.

13. The method of claim 12, wherein at least a portion of said preloaded test substrate has a modified surface.

14. The method of claim 13, wherein said modified surface is modified using plasma etching.

15. The method of claim 13, wherein said modified surface is modified using at least one coating, wherein said coating is a static coating, dynamic coating, or combinations thereof.

16. The method of claim 15, wherein at least one static coating is selected from the group consisting of polyethylene glycol (PEG), collagen, and combinations thereof.

17. The method of claim 15, wherein at least one dynamic coating is selected from the group consisting of polyethylene glycol (PEG), sodium deoxycholate, and combinations thereof.

18. The method of claim 12, wherein said plurality of LAL-reactive standard concentrations is used to generate a standard curve.

19. The method of claim 12, wherein said preloaded test substrate is a microplate.

20. The method of claim 12, wherein said preloaded test substrate further comprises a barrier material to protect said preloaded test substrate from environmental exposure and surface contamination.

* * * * *